(12) United States Patent
Haas et al.

(10) Patent No.: US 7,022,950 B2
(45) Date of Patent: *Apr. 4, 2006

(54) THERMAL WARMING DEVICES

(76) Inventors: William S. Haas, 4615 Ducharme, Bartonville, IL (US) 61607; William J. Haas, 1801 Trail Ridge, Flower Mound, TX (US) 75028

( * ) Notice: Subject to any disclaimer, the term of this patent is extended or adjusted under 35 U.S.C. 154(b) by 0 days.

This patent is subject to a terminal disclaimer.

(21) Appl. No.: 10/854,838

(22) Filed: May 27, 2004

(65) Prior Publication Data

US 2004/0256381 A1    Dec. 23, 2004

Related U.S. Application Data

(63) Continuation-in-part of application No. 10/115,846, filed on Apr. 3, 2002, now Pat. No. 6,770,848.

(60) Provisional application No. 60/494,023, filed on Aug. 11, 2003, provisional application No. 60/473,349, filed on May 27, 2003, provisional application No. 60/284,837, filed on Apr. 19, 2001.

(51) Int. Cl.
*H05B 3/34* (2006.01)

(52) U.S. Cl. ............... 219/528; 219/212; 219/217

(58) Field of Classification Search .......... 219/211, 219/212, 217, 219, 527–530, 535, 539, 522, 219/543, 548, 549; 607/96, 108–111; 338/307, 338/314

See application file for complete search history.

(56) References Cited

U.S. PATENT DOCUMENTS

| | | | |
|---|---|---|---|
| 761,250 A | 5/1904 | Porter | |
| 2,076,382 A | 4/1937 | Minton | |
| 2,342,744 A | 2/1944 | McCready | |
| 2,380,346 A | 7/1945 | Thomlinson | |
| 2,566,349 A | 9/1951 | Mager | |
| 2,738,408 A | 3/1956 | Cheviron | |
| 2,893,639 A | 7/1959 | Martin | |
| 3,007,070 A | 10/1961 | Cargill, Jr. | |
| 3,164,715 A | 1/1965 | Cotts | |
| 3,275,803 A | 9/1966 | True | |
| 3,310,703 A | 3/1967 | Brooks | |
| 3,317,722 A | 5/1967 | Whitney | |
| 3,417,229 A | 12/1968 | Shomphe et al. | |
| 3,422,244 A | 1/1969 | Lauck, III | |
| 3,514,581 A | 5/1970 | Rocholl et al. | |
| 3,808,403 A | 4/1974 | Kanaya et al. | |
| 3,878,362 A | 4/1975 | Stinger | |
| 3,892,947 A | 7/1975 | Strengholt | |
| 3,989,924 A | 11/1976 | Kurtzer | |

(Continued)

FOREIGN PATENT DOCUMENTS

DE    4140507    4/1993

(Continued)

OTHER PUBLICATIONS

Frank, Steven M. et al.: Perioperative Maintenance of Normothermia Reduces the Incidence of Morbid Cardiac Events. JAMA: 1127-1134, Apr. 1997.

(Continued)

*Primary Examiner*—Tu Hoang
(74) *Attorney, Agent, or Firm*—Barnes & Thornburg LLP

(57) ABSTRACT

A heating article including a covering and a thermal warming device for generating heat in the heating article. The covering may be in the form of a blanket or an article of clothing. The covering and the thermal warming device may be separable from each other. The covering may be disposable or reusable. The thermal warming device may be reusable.

32 Claims, 7 Drawing Sheets

U.S. PATENT DOCUMENTS

| | | |
|---|---|---|
| 4,042,803 A | 8/1977 | Bickford |
| 4,139,763 A | 2/1979 | McMullan et al. |
| 4,195,431 A | 4/1980 | Neufeld |
| 4,198,562 A | 4/1980 | Mills et al. |
| 4,250,398 A | 2/1981 | Ellis et al. |
| 4,270,040 A | 5/1981 | McMullan et al. |
| 4,279,255 A | 7/1981 | Hoffman |
| 4,293,763 A | 10/1981 | McMullan |
| 4,335,725 A | 6/1982 | Geldmacher |
| 4,358,668 A | 11/1982 | McMullan et al. |
| 4,429,215 A | 1/1984 | Sakai et al. |
| 4,459,466 A | 7/1984 | Nakagawa |
| 4,504,191 A | 3/1985 | Brown |
| 4,507,877 A | 4/1985 | Vaccari et al. |
| 4,626,664 A | 12/1986 | Grise |
| 4,647,337 A | 3/1987 | Simopoulos |
| 4,713,531 A | 12/1987 | Fennekels et al. |
| 4,782,213 A | 11/1988 | Teal |
| 4,908,497 A | 3/1990 | Hjortsberg |
| 4,912,306 A | 3/1990 | Grise et al. |
| 5,051,654 A | 9/1991 | Nativi et al. |
| 5,148,002 A | 9/1992 | Kuo et al. |
| 5,206,476 A | 4/1993 | Fresch et al. |
| 5,300,101 A | 4/1994 | Augustine et al. |
| 5,300,102 A | 4/1994 | Augustine et al. |
| 5,350,417 A | 9/1994 | Augustine et al. |
| 5,405,371 A | 4/1995 | Augustine et al. |
| 5,444,930 A | 8/1995 | Loew |
| 5,491,377 A | 2/1996 | Janusauskas |
| 5,518,561 A | 5/1996 | Rosa |
| 5,572,817 A | 11/1996 | Chien |
| 5,667,417 A | 9/1997 | Stevenson |
| 5,714,738 A | 2/1998 | Hauschulz et al. |
| 5,845,425 A | 12/1998 | Leake et al. |
| 5,856,031 A | 1/1999 | Burrows |
| 5,891,189 A | 4/1999 | Payne, Jr. |
| 5,902,688 A | 5/1999 | Antoniadis et al. |
| 6,034,353 A | 3/2000 | Demeester |
| 6,051,820 A | 4/2000 | Poix et al. |
| 6,078,026 A | 6/2000 | West |
| 6,189,487 B1 | 2/2001 | Owen et al. |
| 6,203,291 B1 | 3/2001 | Stemme et al. |
| 6,205,690 B1 | 3/2001 | Heropoulos et al. |
| 6,213,616 B1 | 4/2001 | Chien |
| 6,234,641 B1 | 5/2001 | Ungrad |
| 6,271,631 B1 | 8/2001 | Burrows |
| 6,331,695 B1 | 12/2001 | West |
| 6,424,088 B1 | 7/2002 | Murasko |
| 6,683,289 B1 * | 1/2004 | Whitmore et al. .......... 219/730 |

FOREIGN PATENT DOCUMENTS

| | | |
|---|---|---|
| FR | 2041047 | 1/1971 |
| FR | 2577390 | 8/1986 |
| FR | 2769507 | 4/1996 |
| JP | 8106895 | 4/1996 |

OTHER PUBLICATIONS

Cheney, Frederick W.: Should Normothermia be Maintained During Major Surgery? JAMA, 14:277, 1165-1166, Apr. 1997.

Kurz, Andrea.: Perioperative Normothermia to Reduce the Incidence of Surgical-Wound Infection and Shorten Hospitalization. New England Journal of Medicine, 19:334, 1209-1215, May 1996.

Sessler, Daniel I.: Mild Perioperative Hypothermia. New England Journal of Medicine, 24:336, 1730-1737, Jun. 1997.

* cited by examiner

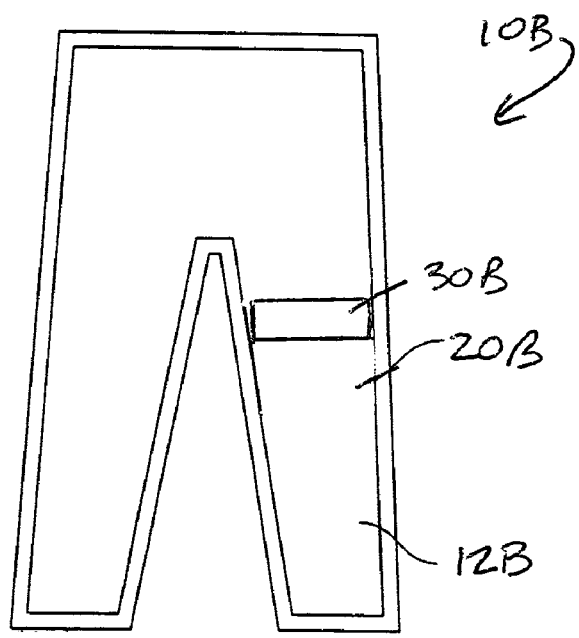
FIG. 10
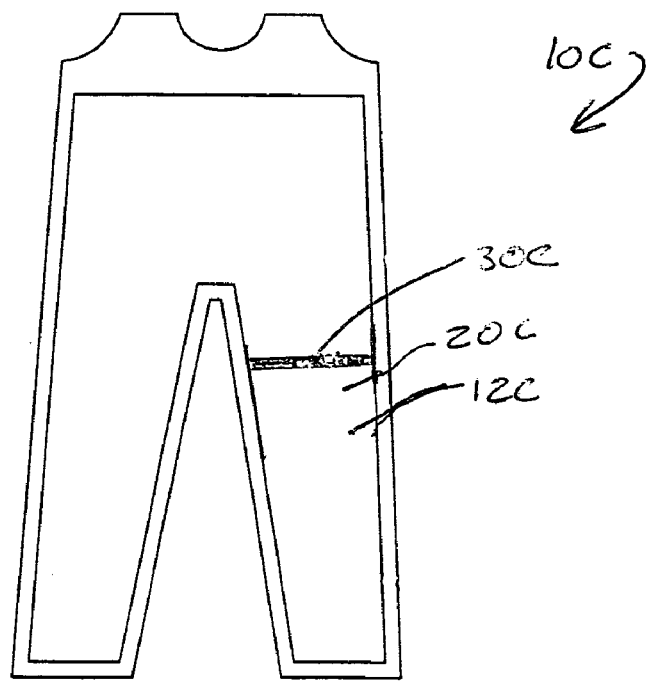

THERMAL WARMING DEVICES

CROSS-REFERENCE TO RELATED PATENT APPLICATION

This is a continuation-in-part of patent application Ser. No. 10/115,846 filed Apr. 3, 2002 now U.S. Pat. No. 6,770,848 which claims priority to provisional application Ser. No. 60/284,837 filed Apr. 19, 2001 and also claims the benefit of priority of provisional patent application Ser. No. 60/473,349 filed May 27, 2003; and the present application further claims priority to provisional patent application Ser. No. 60/494,023 filed Aug. 11, 2003. The disclosures set forth in the referenced applications are incorporated herein by reference in their entirety

FIELD

This invention relates generally to heating articles and, more particularly, to heating articles in the form, for example, of blankets and clothing.

BACKGROUND

Heating blankets including heating devices for generating heat to warm blankets are known in the art. U.S. Pat. Nos. 6,078,026 and 6,331,695 to Wesco provide examples of heating blankets known in the art. It is also known to include heating devices in clothing for generating heat to warm the clothing.

The present disclosure relates to a heating article including a covering and a thermal warming device for generating heat to warm the covering. The covering may, for example, be in the form of a blanket or an article of clothing. The covering and the thermal warming device may be separable from each other. The covering may be disposable or reusable. The thermal warming device may be reusable.

DESCRIPTION OF THE DRAWINGS

FIG. 10 is a plan view of a heating article in accordance with an other embodiment illustrating the covering in the form of pants, the covering shown in broken view to illustrate the heating element; and FIG. 11 is a plan view of a heating article similar to the heating article of FIG. 10, except that the means for opening and closing the pocket of the covering includes a zipper.

DETAILED DESCRIPTION

Figure 1:
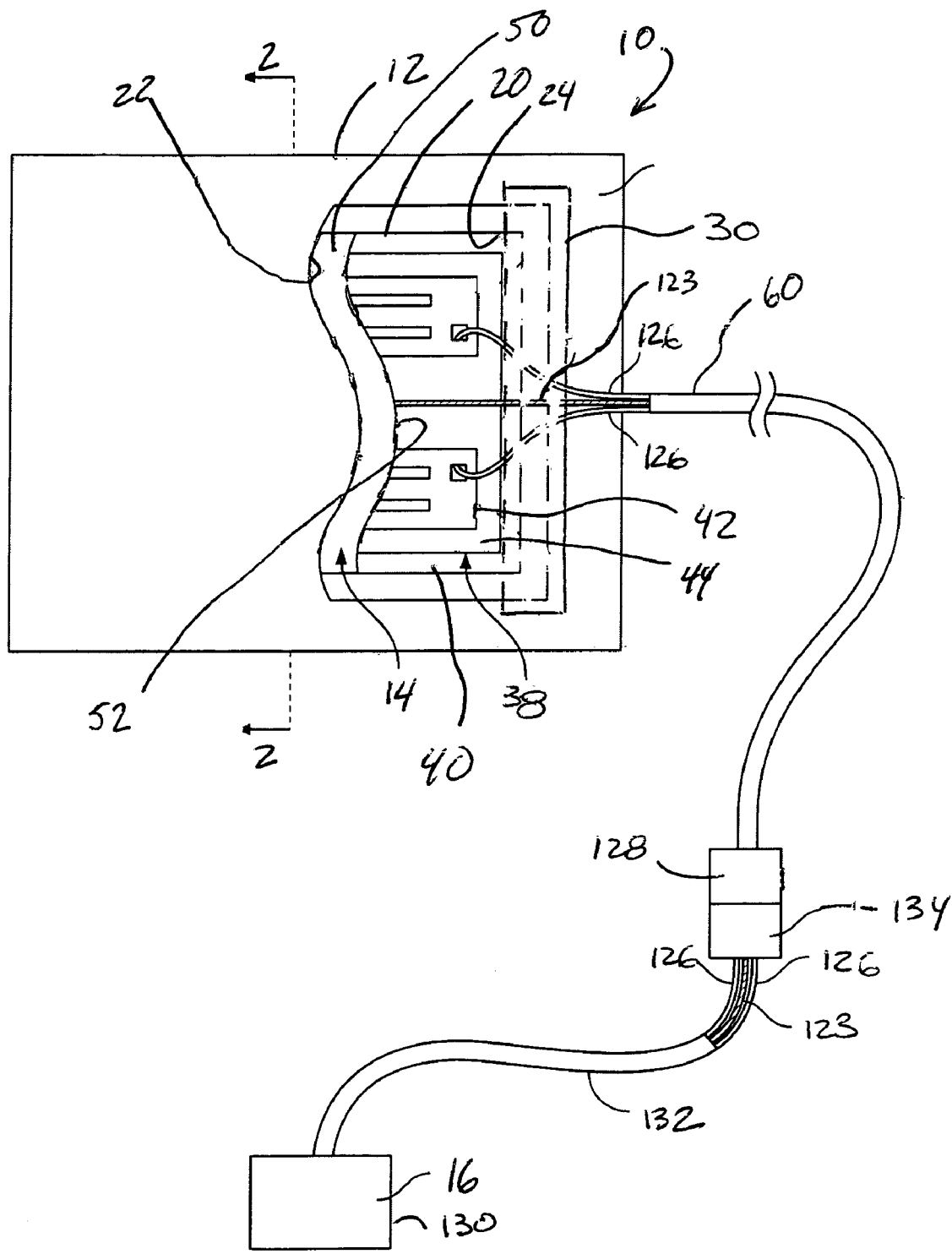
FIG. 1 is a top plan view of a heating article in accordance with an embodiment showing in broken view the covering and the pouch of the thermal warming device to illustrate the heating element.
Figure 2:
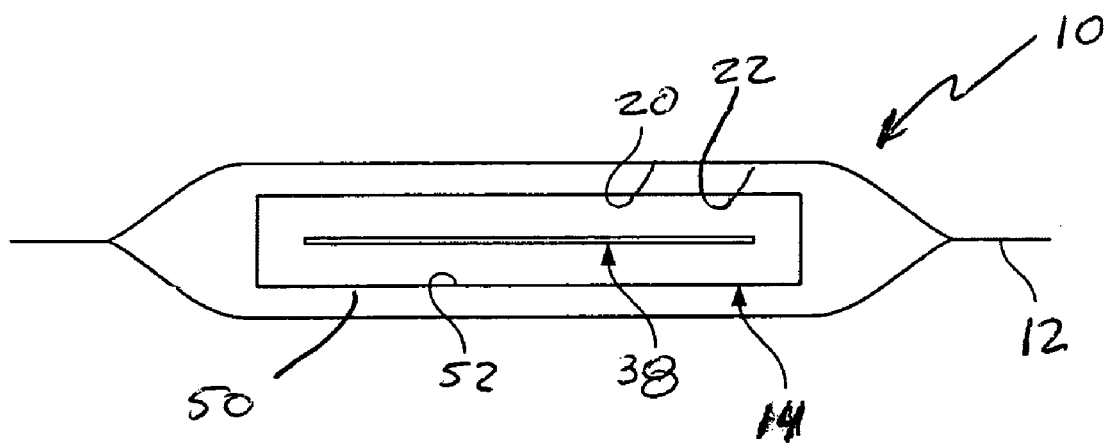
FIG. 2 is a section view taken along the lines 2—2 of FIG. 1.

While the present disclosure may be susceptible to embodiment in different forms, there is shown in the drawing, and herein will be described in detail, an embodiment with the understanding that the present description is to be considered an exemplification of the principles of the disclosure and is not intended to limit the disclosure to the details of construction and the arrangements of components set forth in the following description or illustrated in the drawing.

FIGS. 1–6 illustrate generally a heating article 10 including a covering 12, a thermal warming device 14, and a power source 16. The covering 12 may have any suitable application and any suitable construction and configuration. The covering 12, illustrated in FIG. 1, for example, is in the form of a blanket that may have any suitable application, including, for example, hospital or medical uses, emergency use, individual use or domestic use. It may instead have any other suitable use including, for example, industrial, business, food service or residential application. The covering in accordance with the present disclosure may instead, for example, be in the form of an article of clothing as described below.

The covering 12 illustrated in FIG. 1 has a rectangular configuration and may be sized based on the intended use for the covering. The covering 12 may be disposable or reusable and may be constructed of any suitable material depending on the application and the desired life of the covering 12. For example, if the covering 12 is intended for medical use and to be disposable, it may be constructed of non-woven polypropylene base fabric such as is employed in disposable surgical drapes and gowns or any other suitable material that satisfies these objectives. It may, for example, be constructed of Spunbond/Meltblown/Spunbond (SMS) fabric, made by Kimberly-Clark, Boswell, Ga. It may be constructed of any other suitable disposable material, including, for example, paper or cloth. If the covering 12 is intended to be reusable it may be constructed of any other materials that may be used to construct blankets. Similarly, if the covering 12 is intended for any other domestic or industrial use, it may be constructed of other material that may be used in connection with such use.

The covering 12 includes a pocket 20 which defines a pocket cavity 22 for removably receiving the thermal warming device 14, and a pocket mouth or opening 24 contiguous with the pocket cavity for receiving the thermal warming device into the pocket cavity. The covering 12 also includes means for opening the pocket opening 24 and for closing the pocket opening to enclose the pocket cavity 22. The pocket 20 may have any suitable construction and configuration. The pocket 20 may be and constructed in any suitable manner and may have any suitable size and configuration. The pocket 20 may also be disposed at any suitable covering location. Additionally, each covering 12 may have one or more additional pockets.

The illustrated opening and closing means is in the form of a flap 30.

Accordingly, the thermal device 14 may be inserted through the pocket opening 24 and into the pocket cavity 22 when the flap 30 is in the open position, and the flap can thereafter be closed to enclosing the pocket cavity. The flap 30 may have any suitable construction.

The opening and closing means may include any other suitable construction in accordance with other embodiments. For example, the opening and closing means may include means for releasably retaining the flap 30 in the closed position including, for example, a zipper, a pressure lock, Velcro, buttons, snaps, buttons, staples, string, tie, clips, clasps, tape, etc. Additionally, the opening and closing means may instead omit the flaps and include any suitable structure to open and close the pocket opening 24, including, for example, a zipper (see, e.g., FIG. 11), a pressure lock Velcro, snaps, buttons, staples, string, tie, clips, clasps, tape, etc.

When the pocket opening 24 is closed, the pocket cavity 22 is enclosed such that the thermal warming device 14 does not pass back through the pocket opening. The covering 12, however, may define other openings contiguous with the pocket cavity 22 apart from the pocket opening 24, including, for example, openings for receiving conduit or the like, and that remain open even when the pocket cavity is enclosed by the opening and closing means.

The thermal warming device 14 may have any suitable configuration and structure. The illustrated thermal warming device 14, for example, comprises a heating element 38, in the form of a substrate 40 and a conductive ink 42 or other conductive fluid or other material printed or otherwise affixed to one of the sides 44 of the substrate, and a pouch 50 defining a pouch cavity 52 receiving the substrate. The substrate 40 may be comprised of any suitable material, such as, for example, acetate or Mylar, or Liquixflex, and may have any suitable construction and configuration.

The conductive ink 42 may be UV Ink, made by Allied PhotoChemical, Kimball, Michigan and, in particular, for example, FD 3500 CL UV Ink, which is 100% UV curable. The UV Ink may be light curable by the process called photopolymerization.

Any other suitable conductive ink or any other material may be used such as, for example, a solvent based ink, conductive foils and woven fabrics that conduct heat. The conductive ink 42 or other conductive material generates heat when power is supplied thereto.

The conductive ink 42 can be configured on the substrate 40 in any suitable manner, such as, for example, the configuration illustrated in FIGS. 1–6. In the illustrated embodiment, the conductive ink 42 forms a circuit and the power source provides a current to the circuit. As the current travels along the circuit, however, the circuit short circuits to thereby generate heat. The ink and the electronics can perform in any other suitable manner to generate heat in any suitable manner in accordance with other embodiments.

The ink 42 may be printed onto the substrate 40 in any suitable manner including, for example, a conventional printing press or a screen printing press. The process for affixing the conductive ink 42 to the substrate 40 to construct the heating element 38 may include creating a pattern of lines using a computer and a computer aided drawing program. The final drawing information may then used to generate a film positive, which may transfer to a screen, stencil material, or printing plate. The screen, stencil material, or printing plate may be used to apply the conductive ink 42 to the substrate 40. The application of the conductive ink 42 can be done in any other suitable manner such as, for example, by hand, or automatically, by using a printing press.

Once the conductive ink 42 is applied to the substrate 40, UV light may be used to cure, set, and harden the conductive ink 42. Once the conductive ink 42 is cured to the substrate 40, the heating element 38 may be connected to a temperature controller 130.

The pouch cavity 52 may be sealed or otherwise substantially enclosed. The pouch 50 may instead also define a pouch opening contiguous with the pouch cavity 52 for receiving the substrate into the pouch cavity, and may also include means for opening the pouch opening and for closing the pouch opening to enclose the pouch cavity 52. Any such opening and closing means in connection with the pouch opening may have any suitable construction and configuration including, for example, any of the opening and closing means described above in connection with the covering opening. The pouch 50 may be constructed of any suitable material such as, for example, Liquiflex or any other suitable material.

If the pouch is sealed, the user may dispose of the pouch 50 and reuse the heating element 38 by unsealing the pouch 50 or otherwise opening the pouch cavity 52, removing the heating element 38, and placing the heating element 38 within a new pouch 50. Once the heating element is sealed within the new pouch 50 or otherwise disposed within the pouch cavity 52 of the new pouch, the pouch 50 may be placed inside the pocket 20 within the covering 12.

The heating article may also include a temperature controller connector 60 attached to the conductive ink 42 and to the power source 16. In the embodiment of FIG. 1, the heating element 38, with the temperature controller connector 60 attached, may be placed within the pouch 50. The pouch 50 is then hermetically sealed. This allows for reuse of the heating element 38 and the pouch 50.

The power source 16 may be in any suitable form. The illustrated power source 16 connects to the conductive ink 42 to supply power for heating the heating element 38 to approximately +100 degrees Fahrenheit. The power source 16 illustrated in FIG. 1 is integrated with a temperature controller 130, which regulates the power source 16 by controlling the amount of current supplied to the conductive ink 42 and thereby regulates the temperature of the heating element 38. The temperature controller 130 electrically connects to the conductive ink 42 via a temperature cable 132, as shown, for example, in FIG. 7. The temperature cable 132 connects to the temperature controller connector 60. The r60 connects to the conductive ink 42.

The power source 16 may be DC, AC, solar power, or any other source that may be converted into direct current power and supplied to the conductive ink 42. In the embodiment of FIG. 1, the power source 16 is either a single or dual Ni-MH battery pack, made by AVT, Inc, and integrated with the temperature controller 130. Each individual pack may consist of twelve +1.2 volt cells in series to yield an overall voltage of +14.4 VDC rated at 6.8 amp-hours. The combined capacity of both battery packs yields 14–16 hours of use or 8–10 hours with a single battery pack.

The power source 16 may instead be in the form of battery packs, charged by a battery charger, such as, for example, a Texas Instruments, Inc. Model DV2005S1 Series.

The battery charger receives its power from a boost converter that steps up the volt output of the internal power supply. This higher voltage is required in order to properly charge the twelve cell battery pack. The battery charger also incorporates safety features that will terminate the charge cycle if the battery temperature, maximum charge time and maximum voltage exceed set limits.

The capacity of the power source 16 may be determined by measuring the voltage and displaying the results visually through use of a capacity meter, made by WJH Engineering part number 58-90001000-000. The capacity meter utilizes a National Semiconductor device (LM3419) that is designed to drive a series of five LEDs indicating FULL, {fraction (¾)}, {fraction (½)}, {fraction (¼)} or EMPTY battery. When the capacity of the power source 16 drops below the minimum set threshold an alarm sounds. The capacity meter is electrically removed from operation when the temperature controller 130 turns off the power source 16, this keeps the battery packs from self-discharging.

The power source 16 may alternatively be an AC source. The temperature controller 130 may contain a switching power supply that is capable of operating from 85 to 250 VAC at a rated output of 15 VDC@7 amps. The switching power supply also provides the power to charge the internal battery pack(s). The power source 16 may alternatively be a DC source, the temperature controller 130 may operate from +12 to +16 VDC source such as a vehicle cigarette lighter or from a DC source within an emergency vehicle.

The temperature controller 130 is a device that is preferably used to accurately control the temperature of the heater element 10 to +100+/−4 degrees Fahrenheit. Alternatively, the temperature controller 130 may regulate the temperature of the blanket 50 or article of clothing 60a, 60b, and 60c. The temperature controller 130 consists of the following major components.

The temperature controller 130 may include a proportional integral derivative (PID) controller, made by Oven Industries part number 5C7-362, that is capable of operating in P, PI, PD or PID control. The PID controller is capable of allowing the heating element 38 to be heated to +100 degrees Fahrenheit within 2 minutes. After the first heating of the heater element 10, subsequent heatings of the heating element 38 occur much more quickly. This PID controller is programmable via an RS232 communication port for direct interface with a compatible PC. The RS 232 communications interface has 1500 VAC isolation from all other electronic circuitry minimizing interferences from noise or errant signals caused by common ground loops. This controller will accept a communications cable length in accordance with RS232 interface specifications. Once the desired set parameters are established, the PC may be disconnected and all parameter settings are retained in non-volatile memory. The output signal to the heater element 10 is Pulse Width Modulated and is PC selectable for either 675 Hz or 2700 Hz operation. Pulse Width Modulation averages the amount of energy provided to the heater element 10 and reduces the extreme temperature excursions experienced with an "on/off" system. This tends to extend the life and reliability of the battery source. The PWM control scheme affords control accuracy to within +/−0.05.degree. C. at the control sensor.

The temperature controller 130 may utilize a thermistor 122. The thermistor 122, or control sensor, for the temperature controller 130 may be a Negative Temperature Coefficient (NTC) Thermistor, made by Panasonic, Inc. part number ERT-D2FHL153S, rated at 15,000 ohms at +25 degree C. To provide accurate control of the temperature at the patient location, the thermistor 122 may be affixed to the heating element 38. The thermistor 122 may instead be attached to the covering.

The temperature controller 130 may incorporate several safety devices to protect the patient from potential injury. If the temperature of the heating element 38 reaches above +104.degree. F. the temperature controller 130 automatically shuts off the power to the heating element 38 and sounds an alarm, made by International Component part number BRP2212L-12-C. The alarm can be programmed to any upper limit and can be reset by the temperature controller 130. The temperature controller 130 can also indicate visually when the temperature of the heating element 38 falls below +98 degree F. or when the temperature is within a programmable target window. The temperature controller 130 will also sound an alarm if the temperature cable 132 becomes disconnected from the temperature controller connector 60 or if the thermistor 122 is at fault and becomes shorted or opened.

There may be different manners for connecting the heating element 38 to the temperature controller 130 and controlling the temperature of the heating element 38 depending on the application. For example, in various medical applications, the temperature of the heating element 38 should be extremely controlled and regulated within +100+/−4 degree F. For individual use, however, the user might desire to control the temperature of the heating element 38 directly and can vary the temperature between +100 and +110 degree F. This latter embodiment will be referred to as the alternate temperature controller 130.

The temperature controller 130 may regulate the temperature of the heating element 38. The temperature controller 130 has a temperature cable 132 which contacts the heating element 38 via the temperature controller connector 60. The temperature controller connector 60 attaches to the heating element 38. In the illustrated temperature controller embodiment, the temperature controller connector 60 comprises heater element wires 126, a thermistor 122, thermistor wires 123, a first heater element contact pad 124, a second heater element contact pad 125, and a first socket 128. The heater element wires 126 are 18 gauge wire. The heater element wire 126 contacts the first heater element contact pad 124 and second heater element contact pad 125. The contact pads 124 and 125 are constructed of copper squares, or may be constructed of other conductive material. In turn, the first heater element contact pad 124 contacts conductive ink 42 and the second heater element contact pad 125 contacts the conductive ink at another location. Adhesive tape, copper rivets, or any other suitable structure may be used to affix the heater element contact pads to the conductive ink pads.

Thermistor wires 123 are soldered to a thermistor 122. Adhesive tape is used to affix the thermistor 122 to the heating element 38. Once the temperature controller connector 60 is affixed to the heating element 38, the temperature controller connector 60 may be attached to the temperature cable 132. In this embodiment, the temperature cable 132 contains a second socket 134 and four wires, two of the wires are heater element wires 126 and the two other wires are thermistor wires 123. When the first socket 128 is affixed to the second socket 134, the temperature controller connector 60 connects to the temperature cable 132. Thus, the power source 16 is connected to the conductive ink 42 and current is allowed to be supplied from the power source 16 to the conductive ink 42 via heating element wires 126. In addition, the temperature controller 130 of FIG. 1 connects to the thermistor 122 via thermistor wires 123. The temperature controller 130 also controls the power source 16 by regulating the amount of power supplied to the conductive ink 42, similar to the temperature controller 130 as discussed above.

Figure 7:
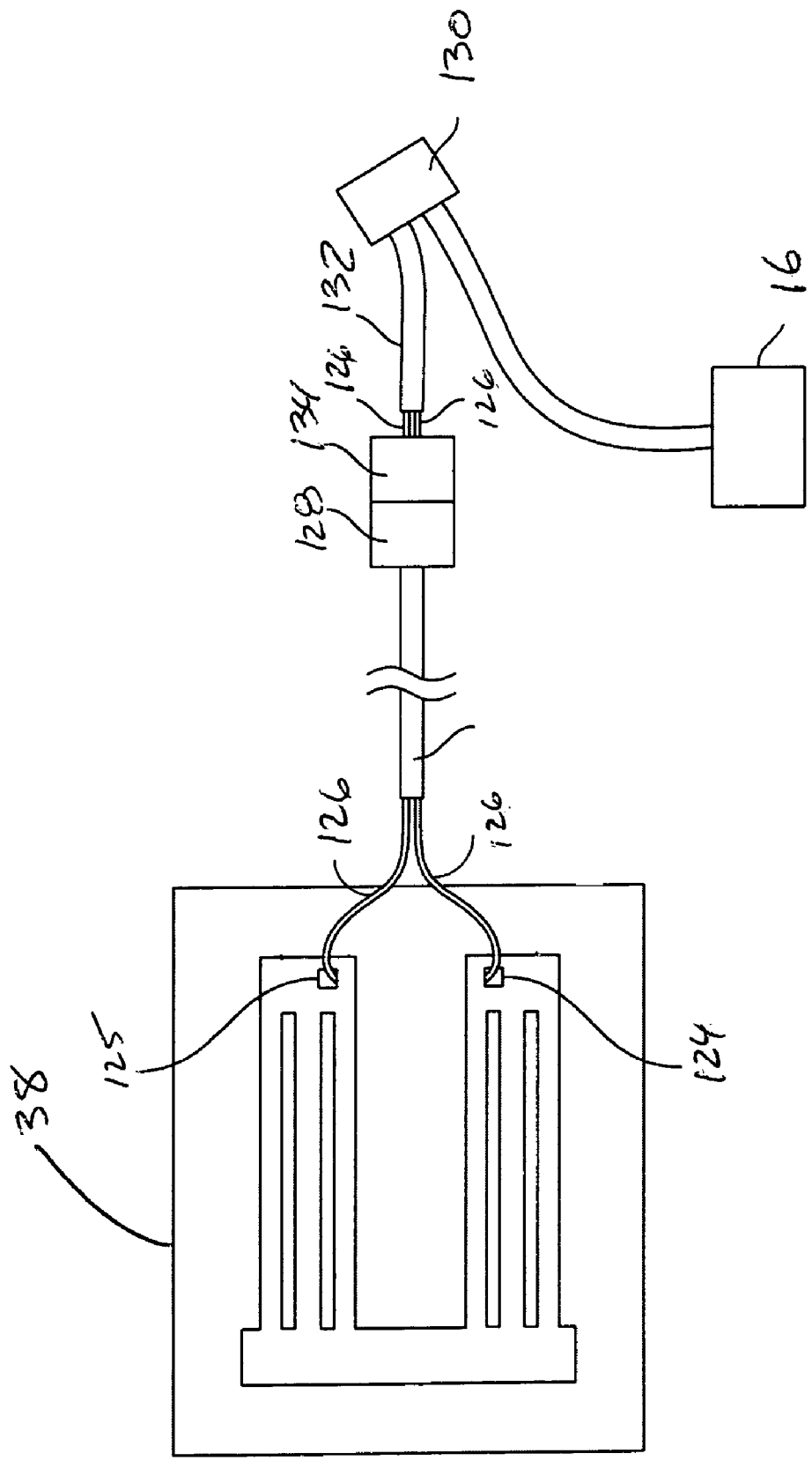
FIG. 7 is a top plan view of a heating article, with the covering and pouch omitted to illustrate the heating element, the power source and the temperature controller in accordance with an other embodiment.
Figure 8:
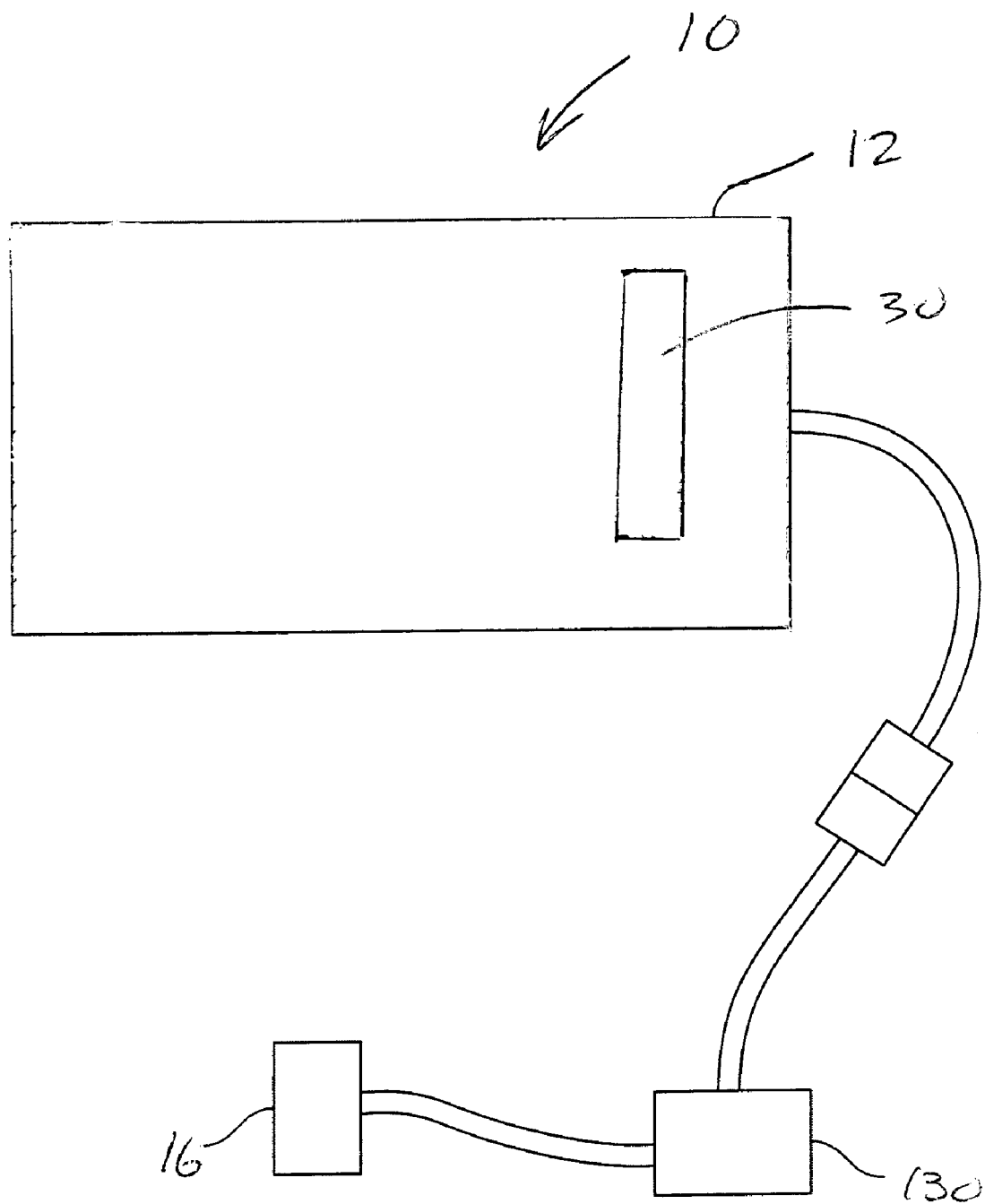
FIG. 8 is a top plan view of a heating article similar to the heating article of FIG. 7.

The alternate temperature controller 130, as shown in FIGS. 7–8, comprises a similar configuration as the temperature controller 130 of FIG. 1, however, it does not encompass a thermistor 122 and thermistor wires 123. An additional difference is that the heating element wires 126 are 22 gauge wire.

The alternate temperature controller 130 does not utilize a thermistor as a feedback for controlling the temperature of the element like the preferred temperature controller 130 does. Instead the user controls the temperature of the heating element 38 by sensing the warmth of the heating element 38 and adjusts a control knob within the alternate temperature controller 130 to achieve the desired comfort. The alternate temperature controller 130 thereby regulates the amount of power supplied by the power source 16 to the conductive ink 42. The alternate temperature controller 130 consists of a solid state switch (MOSFET), a stable timer (NE555), a voltage comparator (LM393), a battery connector, a heating element connector and a control potentiometer with a built in On/Off switch.

The basic design principle is to turn the solid state switch on and off very quickly and vary the current output supplied to the conductive ink 42 by changing the ratio of the "On" time to "Off" time. The ratio is adjustable from 0% (completely turned off) to 100% (completely turned on) by using the control potentiometer to vary the input to the voltage comparator. The variable input voltage is then compared against the output voltage of the timer. Every time the voltage output of the timer crosses the threshold of the compatator the output of the controller turns on and then back off. The frequency of this On/Off cycle is selected to be approximately 300 Hz.

In the alternate temperature controller 130 embodiment, the alternate temperature controller 130 controls a power source 16, which is in the form of a battery, such as, for example, a nickel metal hydride type rechargeable battery, made by AVT, Inc. or a lithium ion battery. A battery charger, such as for example, a XENOTRONIX, Inc. TM. Model MHTX-7 Series, may be used to recharge the battery. Alternatively, in the alternate temperature controller 130, the power source 16 may be a DC source when it is available. The alternate temperature controller 130 is capable of operating from +12 to +16 VDC source such as a vehicle cigarette lighter or from a DC source within an emergency vehicle.

The conductive ink 42 may contact the temperature controller connector 60. The temperature controller connector 60 then is attached to the temperature cable 132 via the first socket 128 and the second socket 134. The temperature cable 132 is attached to the temperature controller containing the power source 16. The preferred temperature controller 130 connects to the thermistor 123 and to the power source 16. The heating element 38, with the temperature controller connector 60 attached, is then placed within a pouch 50 and hermetically sealed. Once the user activates the temperature controller 130, current is supplied from the power source 16 to the heating element 38 and the temperature controller 130 in connection with the thermistor 123 regulates the temperature of the heating element 38. The pouch 50 can then be placed within a pocket 20 of covering 12, or alternatively the pouch 50 may be placed within a pocket within article of clothing.

With the illustrated embodiment, the heating article may be operated as follows. The flap 30 is moved to an open position and the thermal warming device 14 is inserted through the pocket opening 24 and into the pocket cavity 22. The thermal warming device 14 is then secured to the power source with the cables extending from within the cavity to outside the cavity. Activation of the power source causes the thermal warming device 14 to generate heat and warm all or portions of the covering 12. After the initial use, depending upon the construction of the heating article 10 and the extent of the initial use, the heating article can be reused. Instead, the flap 30 can be opened and the thermal warming device 14 can be removed from the pocket cavity 22, so that the covering can be disposed of and the thermal warming device can be used re-used over and over again. Still further, the heating element 38 can be removed from the pouch cavity, so that the pouch 50 can be disposed of and the thermal warming device 14 can be re-used over and over again.

As indicated the above, the covering 12 may be in any suitable form, including, for example, in the form of clothing such as a vest (see, e.g., FIG. 9) or a pair of pants (see, e.g., FIGS. 10–11). The clothing may, of course, be in any other suitable form. The clothing may have any suitable outdoor or other use including, for example, clothing to be worn hunting, fishing, sporting, spectating, construction, or any other outdoor use, such as, for example, any use in connection with emergency, police, military, medical, traffic or similar uses. Additionally, the size, location and number of pockets on the covering may vary.

Figure 9:
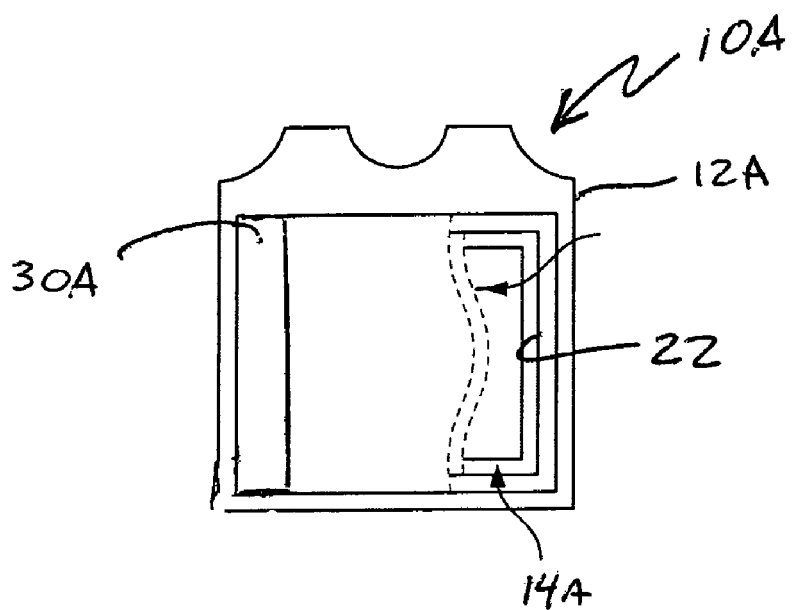
FIG. 9 is a plan view of a heating article in accordance with an other embodiment illustrating the covering in the form of a vest, the covering shown in broken view to illustrate the heating element.
Figure 3:
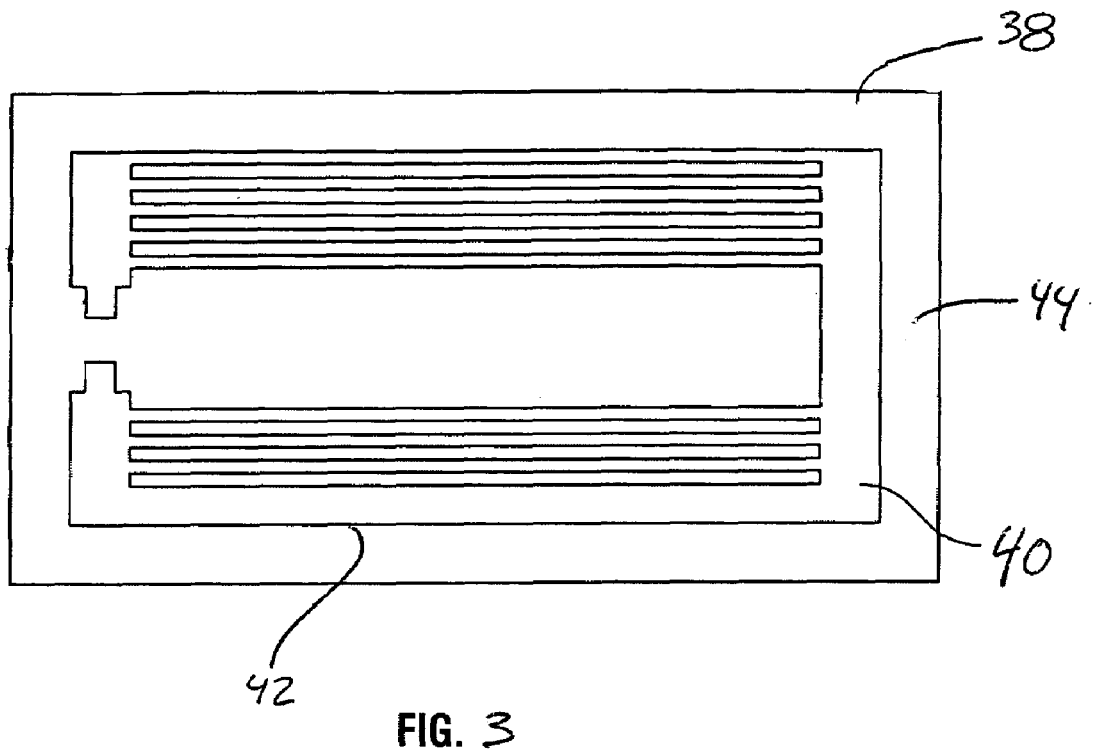
FIG. 3. is a top plan view of the heating element of the heating article of FIG. 1.
Figure 4:
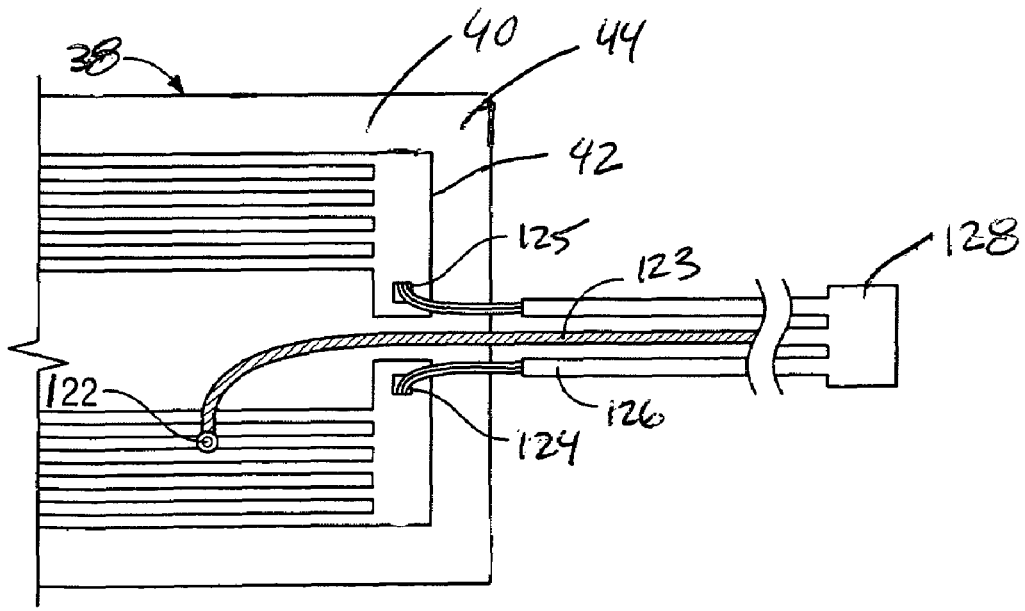
FIG. 4 is a broken top plan view of the heating element of FIG. 3 schematically illustrated connected to a temperature control device.
Figure 5:
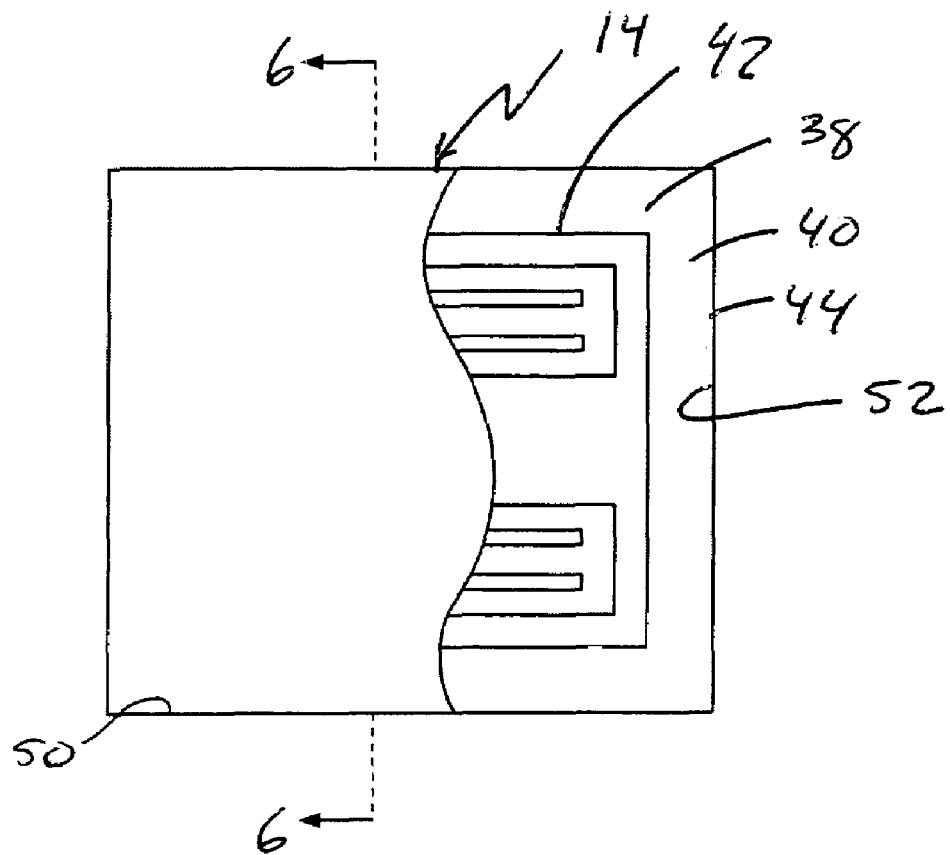
FIG. 5 is a top plan view of a thermal warming device, the pouch being shown in broken view to illustrate the heating element.
Figure 6:
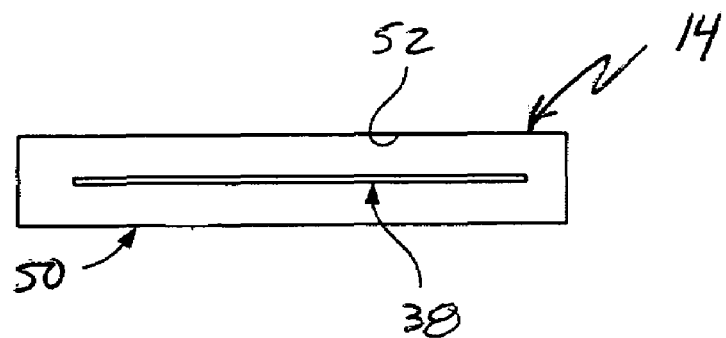
FIG. 6 is a section view taken along the line 6—6 in FIG. 1.

The heating article 10A of FIG. 9 comprises the vest covering 12A having a pocket 20A, and the flap 30A. The heating element (not shown in FIG. 9) is sized to be retained within the pocket cavity. The heating article 10B in FIG. 10 comprises the pants covering 12B having a pocket 20B, and the flap 30B. The heating article 10C in FIG. 11 does not include the flap, but includes a zipper 30C to enclose the pocket cavity. The vest of FIG. 9 and the pants of FIGS. 10–11 may also have one or more pockets in additional locations or in different locations.

While the concepts of the present disclosure have been illustrated and described in detail in the drawings and foregoing description, such an illustration and description is to be considered as exemplary and not restrictive in character, it being understood that only the illustrative embodiment has been shown and described and that all changes and modifications that come within the spirit of the disclosure are desired to be protected by the claims set forth below.

The invention claimed is:

1. A heating article comprising:
   a covering having a pocket defining a pocket cavity and a pocket opening contiguous with the pocket cavity, and means for opening the pocket opening and for closing the pocket opening to enclose the pocket cavity; and
   a thermal warming device configured to generate heat, the thermal warming device removably receivable by the pocket cavity through the pocket opening when the opening and closing means is in an open position, the thermal warming device comprising a pouch defining a pouch cavity and a heating element received by the pouch cavity.

2. The heating article of claim 1 wherein the means for opening and closing the pocket opening includes a flap movable between open and closed positions.

3. The heating article of claim 2 wherein the means for opening and closing the pocket further includes structure for releasably retaining the flap in the closed position.

4. The heating article of claim 1 wherein the means for opening and closing the pocket includes a zipper.

5. The heating article of claim 1 wherein the heating element comprises a substrate and conductive ink affixed to the substrate configured to generate heat.

6. The heating article of claim 1 wherein the covering comprises a blanket.

7. The heating article of claim 6 wherein the blanket is disposable.

8. The heating article of claim 1 wherein the covering comprises an article of clothing.

9. The heating article of claim 8 wherein the article of clothing is disposable.

10. The heating article of claim 1 wherein the heating element is removably received by the pouch cavity.

11. The heating article of claim 1 further comprising a power source electrically connected to the heating element.

12. The heating article of claim 11 wherein the heating element comprises a substrate and conductive ink affixed to the substrate, the power source electrically connected to the conductive ink.

13. The heating article of claim 12 wherein the conductive ink is configured to cause an electric current provided by the power source to short circuit to generate heat.

14. The heating article of claim 1 further including a direct current power source electrically connected to the heating element.

15. The heating article of claim 1 further including a rechargeable battery electrically connected to the heating element.

16. The heating article of claim 1 further including a power source and means for connecting the thermal warming device to the power source.

17. The heating article of claim 16 wherein the connecting means comprises a power cord with a first end attached to the thermal warming device, and a second end detachably connected with the power source.

18. The heating article of claim 1 further comprising means for controlling the temperature of the thermal warming device including a temperature sensing means in communication with the heating element and a temperature controller connected with the temperature sensing means.

19. The heating article of claim 1 wherein the covering is disposable.

20. The heating article of claim 1 wherein the pouch is disposable.

21. The heating article of claim 1 wherein the covering comprises non-woven polypropylene fabric.

22. The heating article of claim 1 wherein the covering comprises a non-flammable material.

23. The heating article of claim 1 wherein the heating element comprises a sheet of acetate and conductive ink affixed thereto.

24. A heating article including:
a covering having a pocket defining a pocket cavity and a pocket opening contiguous with the pocket cavity, and means for opening the pocket opening and for closing the pocket opening to enclose the pocket cavity; and
a thermal warming device removably receivable by the pocket cavity through the pocket opening when the pocket opening is in an open position, the thermal warming device comprising a pouch defining a pouch cavity, a substrate received by the pouch cavity, and conductive ink affixed to the substrate for generating heat.

25. The heating article of claim 24 further comprising a power source electrically connected to the conductive ink.

26. The heating article of claim 25 wherein the conductive ink causes an electric current provided by the power source to short circuit to generate heat.

27. The heating article of claim 24 wherein the means for opening and closing the pocket opening comprises a flap.

28. The heating article of claim 27 wherein the means for opening and closing the pocket opening further comprises structure for releasably retaining the flap in a closed position.

29. The heating article of claim 24 wherein the covering comprises a blanket.

30. The heating article of claim 24 wherein the covering comprises an article of clothing.

31. The heating article of claim 24 further comprising means for controlling the temperature of the thermal warming device.

32. A heating article including:
a covering having a pocket defining a pocket cavity and a pocket opening contiguous with the pocket cavity, and a flap movable between an open position for opening the pocket opening and a closed position for closing the pocket opening to enclose the pocket cavity; and
a thermal warming device removably receivable by the pocket cavity through the pocket opening when the flap is in the open position, the thermal warming device comprising a pouch defining a pouch cavity, a substrate received by the pouch cavity, and conductive ink affixed to the substrate for generating heat; and
a power source electrically connected to the conductive ink.

* * * * *